United States Patent
Blanc et al.

(10) Patent No.: US 12,005,233 B2
(45) Date of Patent: Jun. 11, 2024

(54) AUTOMATED SYSTEM FOR MONITORING A PATIENT'S BLOOD SUGAR

(71) Applicant: Commissariat à l'Énergie Atomique et aux Énergies Alternatives, Paris (FR)

(72) Inventors: Romain Blanc, Grenoble (FR); Eléonore-Maeva Doron, Grenoble (FR); Hector-Manuel Romero Ugalde, Grenoble (FR)

(73) Assignee: Commissariat à l'Énergie Atomique et aux Énergies Alternatives, Paris (FR)

(*) Notice: Subject to any disclaimer, the term of this patent is extended or adjusted under 35 U.S.C. 154(b) by 871 days.

(21) Appl. No.: 17/057,632

(22) PCT Filed: May 3, 2019

(86) PCT No.: PCT/FR2019/051026
§ 371 (c)(1),
(2) Date: Mar. 26, 2021

(87) PCT Pub. No.: WO2019/224447
PCT Pub. Date: Nov. 28, 2019

(65) Prior Publication Data
US 2021/0260285 A1    Aug. 26, 2021

(30) Foreign Application Priority Data
May 22, 2018    (FR) ...................................... 1800493

(51) Int. Cl.
*A61M 5/172*    (2006.01)

(52) U.S. Cl.
CPC ..... *A61M 5/1723* (2013.01); *A61M 2205/502* (2013.01); *A61M 2205/702* (2013.01);
(Continued)

(58) Field of Classification Search
CPC ............ A61B 2562/0219; A61B 5/024; A61B 5/1118; A61B 5/14532; A61B 5/4839;
(Continued)

(56) References Cited

U.S. PATENT DOCUMENTS

2010/0057043 A1* 3/2010 Kovatchev ............. G16H 20/17
                                                    600/301
2015/0217052 A1    8/2015 Keenan et al.

FOREIGN PATENT DOCUMENTS

WO    WO 2018/007161 A1    1/2018

OTHER PUBLICATIONS

International Search Report and Written Opinion for International Application No. PCT/FR2019/051026, dated Aug. 6, 2019.
(Continued)

*Primary Examiner* — Quynh-Nhu H. Vu
(74) *Attorney, Agent, or Firm* — Wolf, Greenfield & Sacks, P.C.

(57) ABSTRACT

An automated system for controlling a patient's blood glucose, including a blood glucose sensor, a device for measuring a physical activity of the patient, and a processing and control unit, wherein: the processing and control unit is configured to generate, by convolution of a signal PA supplied by the device for measuring a physical activity of the patient with a decreasing mathematical function H, a signal IPA representative of the influence of the patient's physical activity on his/her insulin sensitivity; and the processing and control unit is configured to calculate, from a first patient-specific mathematical model fCR and taking into account signal IPA and from a single blood glucose value Gr measured by the sensor, a factor CR representative of the patient's insulin sensitivity.

13 Claims, 4 Drawing Sheets

(52) U.S. Cl.
CPC ... *A61M 2230/06* (2013.01); *A61M 2230/201* (2013.01); *A61M 2230/63* (2013.01)

(58) Field of Classification Search
CPC .............. A61B 5/4866; A61B 5/7275; A61M 2205/502; A61M 2205/702; A61M 2230/201; A61M 2230/63; A61M 5/1723; G16H 20/17; G16H 50/50
See application file for complete search history.

(56) References Cited

OTHER PUBLICATIONS

Jacobs et al., Development of a fully automated closed loop artificial pancreas control system with dual pump delivery of insulin and glucagon. 2011 Annual International Conference of the IEEE Engineering in Medicine and Biology Society (EMBS). Aug. 30, 2011:397-400.

Utz et al. Model of the glucose-insulin system of type-1 diabetics and optimization-based bolus calculation. 2014 UKACC International Conference on Control (Control). Jul. 9, 2014:579-84.

International Preliminary Report on Patentability for International Application No. PCT/FR2019/051026, dated Dec. 3, 2020.

\* cited by examiner

AUTOMATED SYSTEM FOR MONITORING A PATIENT'S BLOOD SUGAR

This application is a national stage filing under 35 U.S.C. § 371 of International Patent Application Serial No. PCT/FR2019/051026, filed May 3, 2019, which claims priority to French patent application FR18/00493, filed May 22, 2018. The contents of these applications are incorporated herein by reference in their entireties.

BACKGROUND

The present disclosure concerns the field of automated blood glucose control systems, and more particularly aims, in such a system, at the determination of a coefficient representative of the patient's insulin sensitivity.

DISCUSSION OF THE RELATED ART

Automated blood glucose regulation systems, also called artificial pancreases, enabling to automatically regulate the insulin inputs of a diabetic patient based on his/her blood glucose history, on his/her meal history, on his/her insulin injection history have already been provided, for example, in French patent application No. 1658881 (B15018/DD16959) filed on Sep. 21, 2016, in French patent application No. 1658882 (B15267/DD17175) filed on Sep. 21, 2016, and in French patent application No. 1756960 (B15860/DD18588) filed on Jul. 21, 2017.

The regulation systems described in the above-mentioned patent applications are MPC-type regulation systems or model-based predictive control systems, where the regulation of the delivered insulin dose takes into account a prediction of the future trend of the patient's blood glucose, obtained from a physiological model describing the assimilation of insulin by the patient's body and its impact on the patient's blood glucose, are here more particularly considered.

More particularly, many automated blood glucose control systems take into account a patient's blood glucose history, meal history, and insulin injection history to determine insulin doses to be delivered to the patient to maintain his/her blood glucose within a desired range.

In automated blood glucose control systems, a parameter which plays an essential role in the determination of the insulin doses to be delivered to the patient is the patient's insulin sensitivity factor, also called compensation sensitivity ratio, or compensation ratio, that is, the quantity of insulin necessary to lower the blood glucose by one gram per liter (in UI/g/l—where UI designates an international insulin unit, that is, the biological equivalent of approximately 0.0347 mg of human insulin).

A problem which is posed is that the insulin sensitivity coefficient may vary significantly from one patient to another, or, for a same patient, according to the patient's conditions, and in particular according to the patient's physical activity.

In practice, known automated blood glucose control systems are based on a fixed insulin sensitivity factor, for example provided by the patient's diabetologist. Short-term variations of the factor are thus not taken into account. As a result, the quantities of insulin injected to the patient are sometimes inadequate, causing a risk of hyperglycemia or of hypoglycemia.

SUMMARY

Thus, an embodiment provides an automated system for controlling a patient's blood glucose, comprising a blood glucose sensor, a device for measuring a patient's physical activity, and a processing and control unit, wherein:

the processing and control unit is configured to generate, by convolution of a signal PA supplied by the device for measuring a physical activity of the patient with a decreasing mathematical function H, a signal IPA representative of the influence of the patient's physical activity on his/her insulin sensitivity; and the processing and control unit is configured to calculate, from a first patient-specific mathematical model $f_{CR}$ and taking into account signal IPA and from a single blood glucose value $G^r$ measured by the sensor, a factor CR representative of the patient's insulin sensitivity.

According to an embodiment, the system further comprises an insulin injection device, and the processing and control unit is configured to control the insulin injection device by taking into account factor CR.

According to an embodiment, the processing and control unit is configured to predict, from a second mathematical model, the future trend of the patient's blood glucose over a prediction period, and to control the insulin injection device by taking the prediction into account.

According to an embodiment, the first mathematical model is a function of equation $$CR = f_{CR}(IPA, G^r) = a \times IPA^b + c \times G^{rd} + e$$

where a, b, c, d, and e are patient-specific parameters.

According to an embodiment, the first mathematical model is a function of equation $$CR = G^r \times f_{CR}(IPA) = G^r \times (a \times IPA^b + c)$$

where a, b, and c are patient-specific parameters.

According to an embodiment, the processing and control unit is configured to implement a step of automatic calibration of first model $f_{CR}$ by taking into account a history of the blood glucose measured by the sensor, a history of insulin injected to the patient, a history of carbohydrate ingestion by the patient, and a history of the patient's physical activity signal PA over a past observation period.

According to an embodiment, the processing and control unit is configured to, during the automatic calibration step, measure a plurality of values of the patient's real insulin sensitivity factor $CR^r$ during a plurality of measurement events contained within the past observation period.

According to an embodiment, each measurement event corresponds to a continuous time range from an initial time $t_{init}$ to a final time $t_{final}$, complying with the following criteria:

time $t_{init}$ is in a hyperglycemia phase, that is, a phase where the patient's blood glucose is greater than a predetermined threshold;

a correction bolus, that is, an additional insulin dose has been delivered to the patient after the beginning of the hyperglycemia phase and before time $t_{init}$, to limit the duration of the hyperglycemia phase;

the patient's blood glucose continuously decreases between initial time $t_{init}$ and final time $t_{final}$; and no carbohydrate ingestion by the patient has occurred between time $t_{init} - T_j$ and time $t_{final}$, where $T_j$ is a predetermined fasting duration.

According to an embodiment, the processing and control unit is configured to, during the automatic calibration step, determine the first mathematical model $f_{CR}$ by regression from said plurality of values of the real insulin sensitivity factor $CR^r$.

According to an embodiment, function H is a decreasing exponential function.

According to an embodiment, the measurement device comprises a user interface via which the patient declares his/her physical activities.

According to an embodiment, the measurement device comprises one or a plurality of sensors capable of measuring quantities representative of the patient's physical activity.

According to an embodiment, the measurement device comprises a motion sensor and/or a heart rate sensor.

BRIEF DESCRIPTION OF THE DRAWINGS

The foregoing features and advantages, as well as others, will be described in detail in the following description of specific embodiments given by way of illustration and not limitation with reference to the accompanying drawings, in which:

FIGS. 4A and 3B are diagrams showing the time variation respectively of a signal PA representative of a patient's physical activity and of a signal IPA representative of the patient's physical activity on his/her insulin sensitivity factor;

DETAILED DESCRIPTION

Figure 1:
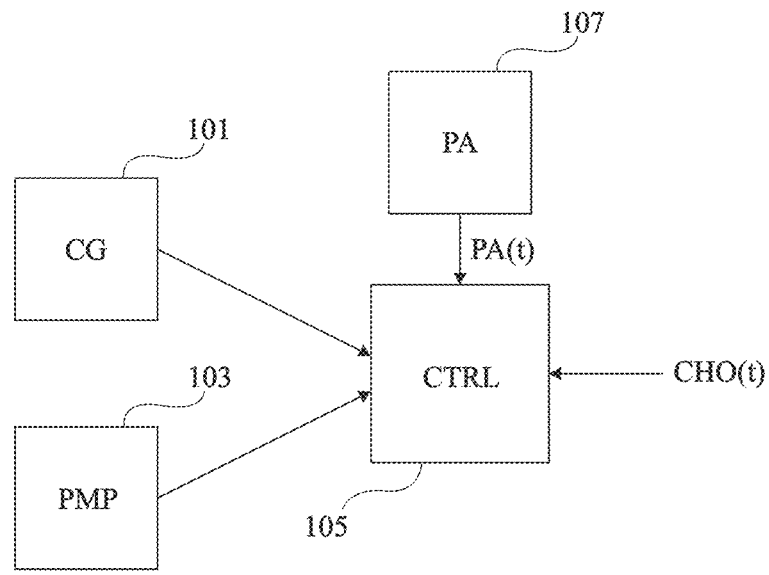
FIG. 1 schematically shows in the form of blocks an example of an automated system for regulating a patient's blood glucose according to an embodiment.

The same elements have been designated with the same reference numerals in the various drawings and, further, the various drawings are not to scale. For the sake of clarity, only the elements that are useful for an understanding of the embodiments described herein have been illustrated and described in detail. In particular, the hardware forming of the control and processing unit of the described systems has not been detailed, the forming of such a control and processing unit being within the abilities of those skilled in the art based on the functional indications of the present description. Further, the blood glucose measurement unit and the insulin injection device of the described systems have not been detailed, the described embodiment being compatible with all or most known blood glucose measurement and insulin injection devices. Unless specified otherwise, the terms "approximately", "substantially", and "in the order of" signify within 10%, preferably within 5%, of the value in question.

FIG. 1 schematically shows in the form of blocks an embodiment of an automated system of regulation of a patient's blood glucose.

The system of FIG. 1 comprises a sensor 101 (CG) capable of measuring the patient's blood glucose. In normal operation, sensor 101 may be permanently positioned on or inside of the patient's body, for example, at the level of his/her abdomen. Sensor 101 is for example a CGM-type ("Continuous Glucose Monitoring") sensor, that is, a sensor capable of continuously measuring (for example, at least once every five minutes) the patient's blood glucose. Sensor 101 is for example a subcutaneous glucose sensor.

The system of FIG. 1 further comprises an insulin injection device 103 (PMP), for example, a subcutaneous injection device. Device 103 is for example, an automatic injection device of insulin pump type, comprising an insulin reservoir connected to an injection needle implanted under the patient's skin, and the pump may be electrically controlled to automatically inject determined insulin doses at determined times. In normal operation, injection device 103 may be permanently positioned inside of or on the patient's body, for example, at the level of his/her abdomen.

The system of FIG. 1 further comprises a processing and control unit 105 (CTRL) connected on the one hand to blood glucose sensor 101, for example, by a wire link or by a radio (wireless) link, and on the other hand to injection device 103, for example, by wire or radio link. In operation, processing and control unit 105 is capable of receiving the data relative to the patient's blood glucose measured by sensor 101, and of electrically controlling device 103 to inject to the patient determined insulin doses at determined times. In this example, processing and control unit 105 is further capable of receiving, via a user interface, not detailed, data CHO(t) representative of the time variation of the quantity of carbohydrates ingested by the patient.

Processing and control unit 105 is capable of determining the insulin doses to be injected to the patient by taking into account, in particular, the history of the blood glucose measured by sensor 101, the history of the insulin injected by device 103, and the history of carbohydrate ingestion by the patient. To achieve this, processing and control unit 105 comprises a digital calculation circuit (not detailed), for example comprising a microprocessor. Processing and control unit 105 is for example a mobile device carried by the patient all along the day and/or the night, for example, a smartphone-type device configured to implement a regulation method of the type described hereafter.

In the example of FIG. 1, processing and control unit 105 is capable of determining the quantity of insulin to be delivered to the patient by taking into account a prediction of the future trend of his/her blood glucose over time. More particularly, processing and control unit 105 is capable, based on the injected insulin history and on the ingested carbohydrate history, and based on a mathematical model, for example, a physiological model describing the assimilation of insulin by the patient's body and its impact on blood glucose, of determining a curve representative of the expected trend of the patient's blood glucose over time, over a period to come called prediction period or prediction horizon, for example, a period from 1 to 10 hours. Taking this curve into account, processing and control unit 105 determines the insulin doses to be injected to the patient during the prediction period to come, so that the patient's real blood glucose (as opposed to the blood glucose estimated based on the physiological model) remains within acceptable limits, and in particular to limit risks of hyperglycemia or of hypoglycemia.

Figure 2:
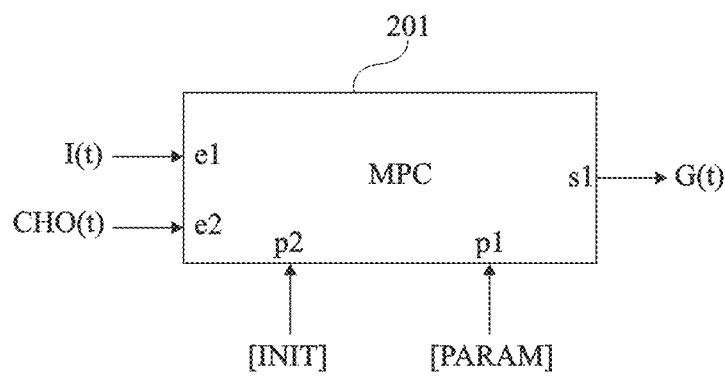
FIG. 2 is a simplified representation of a physiological model used in the system of FIG. 1 to predict the future trend of the patient's blood glucose.

FIG. 2 is a simplified representation of a mathematical model 201 (MPC) used in the system of FIG. 1 to predict the future trend of the patient's blood glucose. In FIG. 2, the model is shown in the form of a processing block comprising:

an input e1 having a signal I(t) representative of the variation, over time t, of the quantity of insulin injected to the patient, applied thereto;

an input e2 having a signal CHO(t) representative of the trend, over time t, of the quantity of carbohydrates ingested by the patient, applied thereto; and an output s1 supplying a signal G(t) representative of the variation, over time t, of the patient's estimated blood glucose.

Mathematical model 201 is for example a physiological model. As an example, model 201 is a compartmental model comprising, in addition to input variables I(t) and CHO(t) and output variable G(t), a plurality of state variables corresponding to physiological variables of the patient, varying over time. The time variation of the state variables and of output variable G(t) is ruled by a differential equation system comprising a plurality of parameters represented in FIG. 2 by a vector [PARAM] applied to an input p1 of block 201. The response of the physiological model is further conditioned by the initial states or initial values assigned to the state variables, represented in FIG. 2 by a vector [INIT] applied to an input p2 of block 201.

As an example, the physiological model 201 used in the system of FIG. 1 is the model called Hovorka model, described in the article entitled "Nonlinear model predictive control of glucose concentration in subjects with type 1 diabetes" of Roman Hovorka et al. (Physiol Meas. 2004; 25:905-920), and in the article entitled "Partitioning glucose distribution/transport, disposal, and endogenous production during IVGTT", of Roman Hovorka et al. (Am J Physiol Endocrinol Metab 282: E992-E1007, 2002). More generally, any other physiological model describing the assimilation of insulin by a patient's body and its effect on the patient's blood glucose may be used.

Among the parameters of vector [PARAM], some may be considered as constant for a given patient. Other parameters, called time-dependent parameters hereafter, are however capable of varying over time. Due to the variability of certain parameters of the system, it is in practice necessary to regularly recalibrate the model used, for example, every 1 to 20 minutes, for example, every 5 minutes, to make sure that the predictions of the model remain relevant. Such an update of the model, called model personalization, should be capable of being automatically carried out by the system of FIG. 1, that is, without requiring physically measuring the time-dependent parameters of the system on the patient and then transmitting them to processing and control unit 105.

Figure 3:
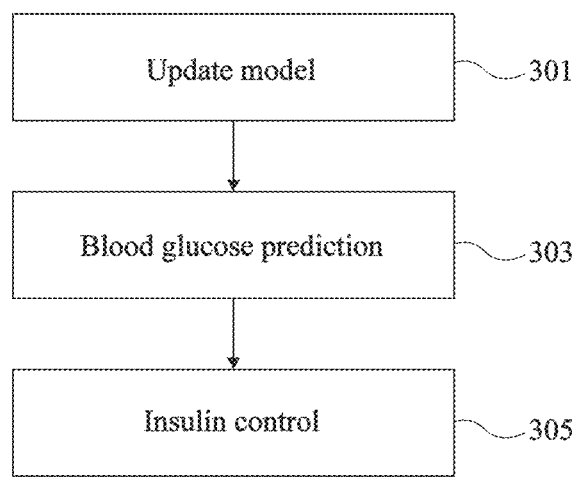
FIG. 3 is a diagram illustrating an example of an automated blood glucose regulation method capable of being implemented by the system of FIG. 1.

FIG. 3 is a diagram illustrating an example of an automated blood glucose regulation method capable of being implemented by the system of FIG. 1.

This method comprises a step 301 of recalibration or update of the model, which may for example be repeated at regular intervals, for example, every 1 to 20 minutes. During this step, processing and control unit 105 implements a method of re-estimation of the time-dependent parameters of the model, taking into account the data relative to the insulin effectively injected by device 103 and the data relative to the real blood glucose measured by sensor 101 for a past observation period of duration ΔT, for example a period from 1 to 10 hours preceding the calibration step. More particularly, during the calibration step, processing and control unit 105 simulates the patient's behavior over the past observation period based on the physiological model (taking into account possible carbohydrate ingestions and insulin injections during this period) and compares the curve of the blood glucose estimated by the model with the curve of the real blood glucose measured by the sensor during this same period. Processing and control unit 105 then searches, for the time-dependent parameters of the model, a set of values leading to minimizing a quantity representative of the error between the blood glucose curve estimated by the model and the real blood glucose curve measured by the sensor during the observation period. As an example, the processing and control unit searches for a set of parameters leading to minimizing an indicator m representative of the area between the curve of the blood glucose estimated by the model and the curve of the real blood glucose measured by the sensor during the observation period, also called standard deviation between the estimated glucose and the real glucose, for example defined as follows:

$$m = \frac{1}{\Delta T} \sum_{t=t_0-\Delta T}^{t_0} |G^r(t) - G(t)|^2$$

where t is a discretized time variable, $t_0-\Delta T$ corresponds to the time of beginning of the past observation phase, $t_0$ corresponds to the end time of the past observation phase (for example corresponding to the time of beginning of the model calibration step), $G^r$ is the curve of time variation of the real blood glucose measured by sensor 101 during period $[t_0-\Delta T, t_0]$, and G is the curve of the blood glucose estimated based on the model during period $[t_0-\Delta T, t_0]$. As a variation, for the calculation of the mean standard deviation, variable ΔT may be replaced with the number of measurements performed during the past observation period. The optimal parameter search algorithm used during this step is not detailed in the present application, the described embodiments being compatible with usual algorithms used in various field to solve problems of parameter optimization by minimization of a cost function.

It should be noted that during step 301, in addition to the time-dependent parameters of the model, processing and control unit 105 defines a vector [INTIT] of initial states (states at time $t_0-\Delta T$) of the state variables of the model, to be able to simulate the patient's behavior from the model. To define the initial states of the state variables of the model, a first possibility comprises making the assumption that, in the period preceding the observation period $[t_0-\Delta T, t_0]$ having the model calibration based thereon, the patient was in a stationary state, with a constant injected insulin flow, and no dietary intake of carbohydrates. Under this assumption, all the derivatives of the differential equation system may be considered as zero at initial time $t_0-\Delta T$. The values at time $t_0-\Delta T$ of the state variables of the system may then be analytically calculated. To improve the initialization, another possibility comprises making the same assumptions as previously, but adding the constraint that the glucose estimated at time $t_0-\Delta T$ is equal to the real glucose measured by the sensor. To further improve the initialization, another possibility is to consider the initial states of the state variables of the model as random variables, just as the time-dependent parameters of the model. The initial states of the state variables are then determined in the same way as the time-dependent parameters of the model, that is, processing and control unit 105 searches for a set of values of initial states [INIT] resulting in minimizing a quantity representative of the error between the curve of the blood glucose estimated by the model and the curve of the real blood glucose during the past observation period.

The method of FIG. 3 further comprises, after step 301, a step 303 of prediction, by processing and control unit 105, of the time variation of the patient's blood glucose over a prediction period to come [$t_0$, $t_0+T_{pred}$] of duration $T_{pred}$, for example, in the range from 1 to 10 hours, based on the physiological model updated at step 301 and taking into account the history of the insulin injected to the patient and the history of carbohydrates ingested by the patient.

The method of FIG. 3 further comprises, after step 303, a step 305 of determination, by processing and control unit 105, by taking into account the future blood glucose curve predicted at step 303, of the insulin doses to be injected to the patient for the prediction period to come [$t_0$, $t_0+T_{pred}$]. At the end of this step, processing and control unit 105 may program injection device 103 to deliver the doses determined during the prediction period [$t_0$, $t_0+T_{pred}$].

Steps 303 of prediction of the blood glucose and 305 of determination of the future doses of insulin to be delivered may for example be repeated at each update of the physiological model (that is, after each iteration of step 301), for each new carbohydrate ingestion notified by the patient, and/or for each new administration of an insulin dose by injection device 103.

According to an aspect of an embodiment, at step 305, processing and control unit 105 estimates the patient's insulin sensitivity factor CR, taking into account the patient's physical activity. For this purpose, as shown in FIG. 1, the system comprises a device 107 for measuring a physical activity of the patient. Device 107 is coupled to processing and control unit 105, for example, by a wire link or a radio link (wireless), and communicates to processing and control unit 105 a signal PA(t) representative of the time variation of a physical activity of the patient. Device 107 is for example a mobile device carried by the patient all along the day and/or the night.

As an example, device 107 is a simple user interface (not detailed) via which the patient declares his/her physical activities. As an example, signal PA(t) corresponds to a level of physical intensity declared by the patient via device 107. Device 107 is for example provided with a keyboard enabling the user to input, on a scale from 0 to N, where N is a positive integer, for example, equal to 3, the intensity level of his/her current physical activity, value 0 corresponding to a physical activity considered as null or negligible, and value N corresponding to the patient's maximum physical activity intensity level.

As a variant, device 107 comprises one or a plurality of sensors capable of measuring quantities representative of the patient's physical activity. As an example, device 107 comprises at least one motion sensor (not detailed in FIG. 1), for example, an accelerometer. Device 107 may further comprise a sensor of the patient's heart rate (not detailed in FIG. 1). In this case, signal PA(t) is for example a signal representative of the patient's energy expenditure, calculated from the output data of the sensor(s) of device 107, for example, as described in the article entitled "Prior automatic posture and activity identification improves physical activity energy expenditure prediction from hip-worn triaxial accelerometry" of M. Garnotel et al. (Journal of Applied Physiology (1985). 2017 Nov. 30), or in the article entitled "An original piecewise model for computing energy expenditure from accelerometer and heart rate signals" of H. Romero-Ugalde et al. (Physiological measurement, 2017 Jul. 28; 38(8):1599-1615).

As a variant, signal PA(t) may be a combination of a signal measured by means of one or a plurality of sensors of device 107, and of a signal of physical activity intensity declared by the patient by means of a user interface of device 107.

According to an aspect of an embodiment, processing and control unit 105 is configured to calculate, from the signal PA(t) representative of the variation, according to time t, of the patient's physical activity, a signal IPA(t) representative of the variation, according to time t, of the influence of the past or current physical activity on the patient's insulin sensitivity factor. More particularly, signal IPA(t) is generated by convolution of signal PA(t) with a decrease function H(t). Function H(t) is for example a decreasing exponential function. More generally, any other decreasing function representative of the decrease of the influence of a physical activity on the patient's insulin sensitivity factor may be used, for example, a decreasing linear function, a phase of decrease of a parabolic or hyperbolic function, etc. Decrease function H(t) may take into account the intensity and the duration of the physical activity, as well as a characteristic decay time $T_{ext}$, that is, a duration beyond which the influence of the past physical activity on the insulin sensitivity factor is considered as null or negligible.

As an example, function IPA(t) is defined as follows:

$$IPA(t)=(PA*H)(t)$$

with:

$$H(t) = \frac{1}{\tau}e^{-\frac{t}{\tau}}$$

where $\tau$ is a variable, in $\min^{-1}$, which is a function of the duration and of the intensity of the past physical activities.

In practice, signal PA(t) and function H(t) may be sampled at a sampling period T, for example, in the order of 1 minute. Variable $\tau$ may be calculated at each time t, over a sliding time window [$t-T_{ext}$; t]. As an example, variable $\tau$ is defined as follows:

$$\tau = \sum_{k=1}^{Next} I(k) \times \left(1 - \frac{k}{N_{ext}}\right)$$

$N_{ext}$ being an integer greater than 1 defining the duration of decay period $T_{ext}$, such that $T_{ext}=N_{ext}\times T$, and I being a vector of $N_{ext}$ values representing the intensity of the physical activity performed by the patient over period [$t-T_{ext}$; t], sampled at sampling period T. As an example, decay period $T_{ext}$ is in the range from 12 to 72 hours, for example, in the order of 48 hours, that is, $N_{ext}=2,880$ for T=1 minute.

Figure 4A:
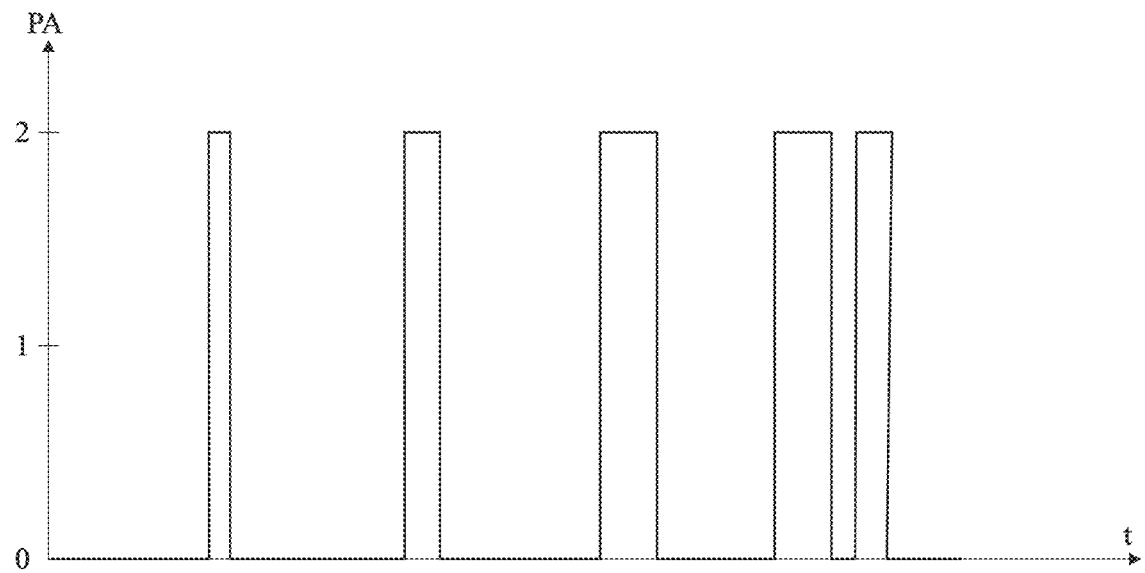
Figure 4B:
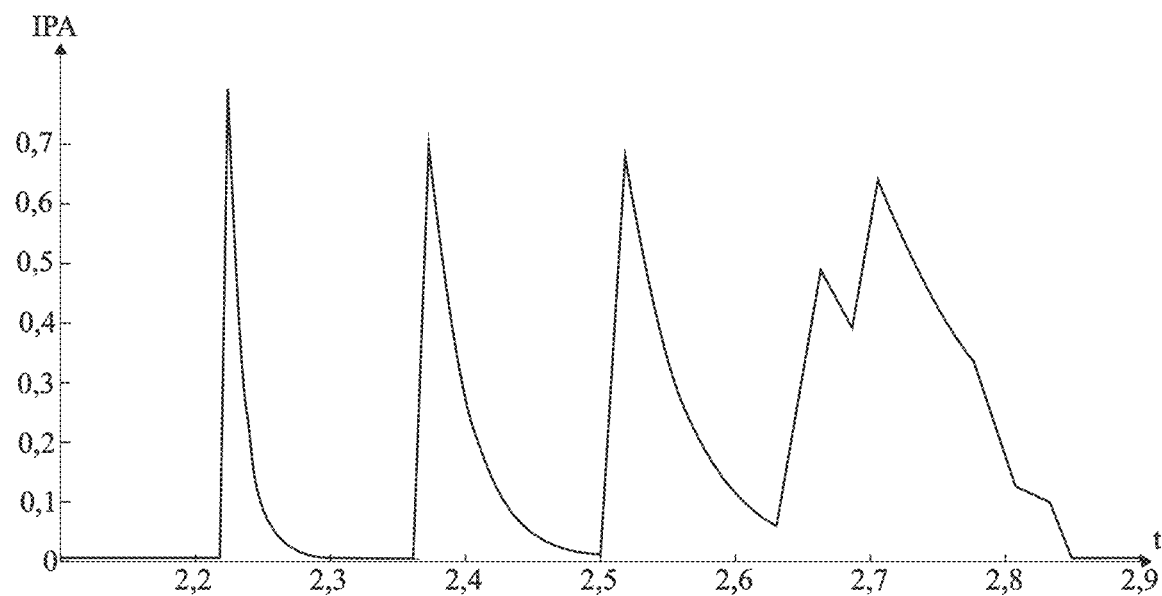

FIGS. 4A and 4B are diagrams showing, as an illustration, the time variations, respectively of signal PA (FIG. 4A) representative of the intensity of a patient's physical activity, and of signal IPA (FIG. 4B) representative of the influence of the patient's physical activity on his/her insulin sensitivity factor. In this example, signal IPA is calculated by the processing and control unit based on the above-defined exponential decrease function H.

According to an aspect of an embodiment, during step 305 of the method of FIG. 3, processing and control unit 105 estimates the patient's insulin sensitivity factor CR from a single value of signal IPA and on a single blood glucose value measured by sensor 101, based on a predetermined mathematical mode. More particularly, at step 305, processing and control unit 105 calculates the patient's estimated insulin sensitivity factor CR from a predetermined mathematical function $f_{CR}$ such that $CR=G^r(t) \times f_{CR}(IPA(t))$, where $G^r(t)$ is the patient's real blood glucose value measured by sensor 101 at a current time t, for example, at time $t=t_0$ of beginning of the prediction period considered at step 303, IPA(t) being the value of signal IPA at time t. At step 305, processing and control unit 105 then determine the future insulin doses to be delivered to the patient by taking into account the sensitivity factor CR thus calculated.

The inventors have shown that there exists, for a given patient, a strong correlation between the time variation of the patient's signal IPA, and the time variation of the patient insulin sensitivity factor, normalized with respect to the patient's blood glucose. The inventors have particularly shown that the real time adjustment of the patient's insulin sensitivity factor according to his/her instantaneous blood glucose and to signal IPA, enables to determine with a better accuracy the future insulin doses to be delivered to the patient and thus to limit risks of hyperglycemia or hypoglycemia.

Figure 5A:
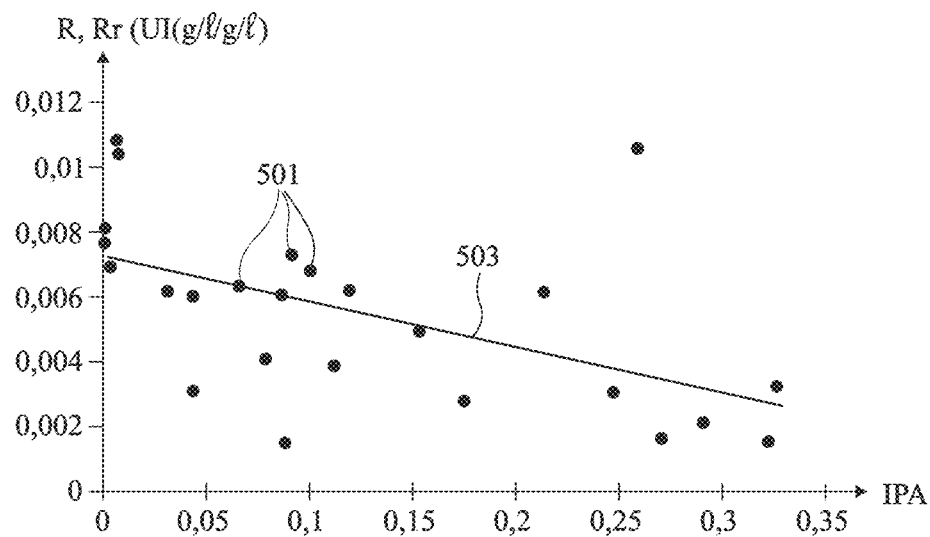
FIGS. 5A and 5B are diagrams showing the variation of a patient's insulin sensitivity factor according to his/her blood glucose and to signal IPA.
Figure 5B:
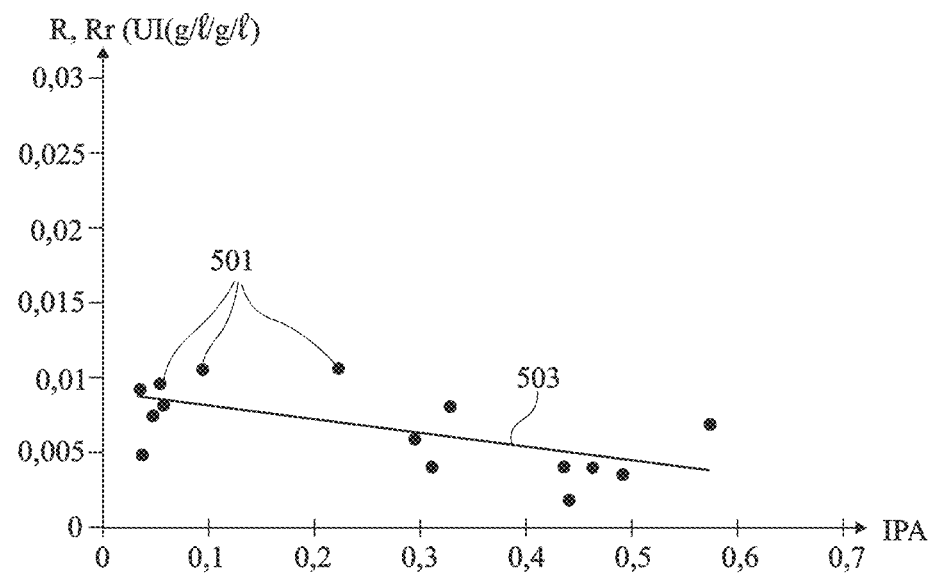

FIGS. 5A and 5B are diagrams respectively showing, for two different patients, the variation of the patient's insulin sensitivity factor divided by his/her blood glucose (in ordinates, in UI/g/l/g/l), according to the value of the patient's variable IPA (in abscissas). Each diagram comprises a plurality of points 501, each corresponding to a measurement of the ratio $R^r=CR^r/G^r$ of the patient's real insulin sensitivity factor $CR^r$ to a corresponding value (that is, correlated in time) of the patient's real blood glucose $G^r$.

The real insulin sensitivity factor $CR^r$ may be measured by any known method of measurement of a patient's insulin sensitivity factor, for example, by methods of the type described in patent applications US2010/0198520, US2013/0211220, and WO2017/040927.

In a preferred embodiment, the patient's real insulin sensitivity factor $CR^r$ is determined from the patient's blood glucose history (for example, measured by sensor 101 in the system of FIG. 1), meal history, and insulin injection history, according to the following method.

Based on the patient's data history, measurement events are identified, that is, time ranges during which the insulin sensitivity factor is isolated, that is, during which a decrease in the patient's blood glucose linked to the delivery of insulin is observed. As an example, the selected events are continuous time ranges from an initial time $t_{init}$ to a final time $t_{final}$, complying with the following criteria:
  time $t_{init}$ is in a hyperglycemia phase, that is, a phase where the patient's blood glucose is greater than a predetermined threshold, for example, in the order of 1.40 g/l;
  a correction bolus, that is, an additional insulin dose, has been delivered to the patient after the beginning of the hyperglycemia phase and before time $t_{init}$, to limit the duration of the hyperglycemia phase;
  the patient's blood glucose continuously decreases between initial time ti t and final time $t_{final}$;
  no carbohydrate ingestion by the patient has occurred between time $t_{init}-T_j$ and time $t_{final}$, where $T_j$ is a predetermined fasting period, for example, greater than or equal to 1 hr and preferably greater than or equal to 2 hrs.

As an example, time $t_{init}$ corresponds to the blood glucose peak of the hyperglycemia phase. Time $t_{final}$ for example corresponds to a time of blood glucose stabilization or rise according to the hyperglycemia phase, or also to a disturbance such as a meal or a carbohydrate ingestion.

For each identified event, the patient's real insulin sensitivity $CR^r$ is calculated as follows:

$$CR^r = \Delta I / \Delta G,$$

where $\Delta I$ designates the quantity of insulin consumed during the event and $\Delta G$ designates the difference between the patient's real blood glucose at time $t_{init}$ of beginning of the event and the patient's real blood glucose at time $t_{final}$ of end of the event. The quantity of insulin $\Delta I$ consumed during the event may for example be calculated by taking into account the insulin doses delivered before and after the event, and the kinetics of absorption of insulin by the body. As an example, the quantity of insulin $\Delta I$ consumed during the event corresponds to the difference between the patient's quantity of insulin on board, that is, the quantity of insulin still active (that is, still capable of having an effect of the blood glucose), at time $t_{init}$ of beginning of the event and the quantity of insulin on board at time $t_{final}$ of end of the event. The determination of the patient's quantity of insulin on board at times $t_{init}$ and $t_{final}$ may be performed by any known method of determination of a patient's quantity of insulin on board. As an example, the determination of the patient's quantity of insulin on board at a time t may be calculated by convolution, over a period from a time preceding time t to time t, of a curve representative of the time variation of the quantity of insulin injected to the patient before time t, and of a function $f_{IOB}$ representative of the kinetics of insulin consumption by the body, for example, function $$f_{IOB}(t) = \left(1 + \frac{t-1}{\tau'}\right) \times e^{-\frac{t-1}{\tau'}},$$

where t is the discretized time variable and $\tau'$ is a time constant of predetermined duration, for example in the range from 40 to 60 minutes, for example in the order of 47 minutes.

For each event, the value of the patient's real blood glucose retained for ratio $R^r$ is for example the real blood glucose value $G^r(t_{init})$ at time $t_{init}$ of beginning of the event.

Thus, for each identified event, ratio $R^r$ is calculated as follows: $R^r=CR^r/G^r(t_{init})$.

For each event, the retained value of signal IPA is for example value $IPA(t_{init})$ at time $t_{init}$ of beginning of the event.

For each patient, to define a patient-specific function or mathematical model $f_{CR}$, a relatively high number of events $Nb_{ev}$ is first identified in the patient's history data, and, for each event, a value of ratio $R^r$ and an associated value of signal IPA are measured. As an example, the number of events $Nb_{ev}$ used to define function $f_{CR}$ is in the range from 20 to 100, for example from 30 to 60, for example in the order of 40. Function $f_{CR}$ is then determined by regression from the $Nb_{ev}$ patient-specific measurement points (the points 501 of FIGS. 5A and 5B). As an example, for each patient, function $f_{CR}$ is obtained by regression from the $Nb_{ev}$ measurement points 501 obtained for the patient. For each patient, function $f_{CR}$ then is a function of equation:

$$f_{CR}(IPA) = a \times IPA_b + c$$

where a, b, and c are patient-specific parameters, parameter b corresponding to the order of the model. As an example, parameter b is set to be equal to 1, the model then being a linear model.

In each of the diagrams of FIGS. 5A and 5B, a line 503 represents the function $f_{CR}$ determined for the patient, linking the patient's variable IPA to the estimated ratio R of his/her insulin sensitivity factor to his/her blood glucose.

As an example, in the system of FIG. 1, function $f_{CR}$ may be determined in automated fashion by processing and control unit 105, during a calibration phase.

Control and processing unit 105 may further be configured to update in automated fashion, for example, periodically, the parameters of function $f_{CR}$, to take into account the new history data recorded by the regulation system along its use by the patient.

In a preferred embodiment, the number $Nb_{ev}$ of events taken into account for each update of the parameters of function $f_{CR}$ remains constant. In other words, each time a new event is taken into account for the update of the parameters of function $f_{CR}$, a previous event, for example, the oldest event, is excluded from the model, which enables for the model not to set and to be able to evolve over time.

Figure 6:
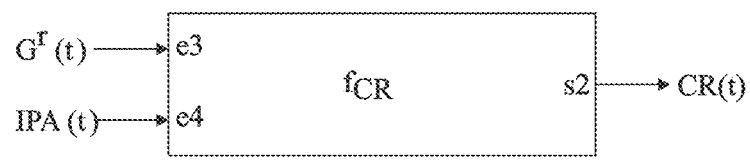
FIG. 6 is a simplified representation of a mathematical model used in the system of FIG. 1 to determine the patient's insulin sensitivity factor.

FIG. 6 is a simplified representation of the mathematical model $f_{CR}$ used in the system of FIG. 1 to determine the patient's insulin sensitivity factor. In FIG. 6, the model is shown in the form of a processing block comprising an input e3 having a signal $G^r(t)$ representative of the patient's real blood glucose, measured by sensor 101, at a measurement time t, applied thereto, an input e4 having the signal IPA(t) calculated by processing and control unit 105 applied thereto, and an output s2 supplying a signal CR(t) representative of the patient's estimated insulin sensitivity factor at time t, such that:

$$CR(t)=G^r(t) \times R(t)=G^r(t) \times f_{CR}(IPA(t))$$

Figure 7:
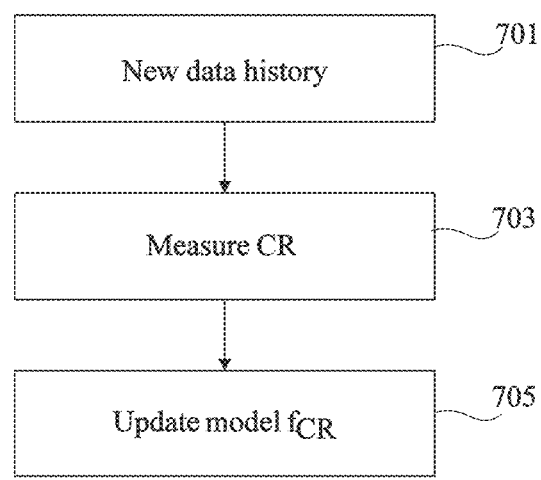
FIG. 7 is a diagram illustrating an example of a method capable of being implemented by the system of FIG. 1 to update the mathematical model of FIG. 6.

FIG. 7 is a diagram illustrating an example of a method capable of being implemented by the system of FIG. 1 to update mathematical model $f_{CR}$ so as to take into account a new data history of the patient.

The method of FIG. 7 comprises a step 701 during which the processing and control unit acquires and stores the real blood glucose data $G^r$ measured by sensor 101, the data of insulin effectively injected by device 103, the data of carbohydrate ingestion by the patient, as well as the physical activity data, over an observation period. The observation period considered at step 701 is selected to comprise at least one event enabling to measure the patient's real sensitivity factor $CR^r$.

The method of FIG. 7 further comprises, after step 701, a step 703 of calculation of the patient's ratio $R^r=CR^r/G^r$ and of the corresponding value of the patient's signal IPA (for example, the value of signal IPA at the beginning of the event having the calculation of ratio $R^r=CR^r/G^r$ based thereon), from the data acquired during the observation period.

The method of FIG. 7 further comprises, after step 703, a step 705 of update of model $f_{CR}$ taking into account the new value of ratio $R^r$ and the corresponding value of signal IPA determined at step 703.

Specific embodiments have been described. Various alterations, modifications, and improvements will readily occur to those skilled in the art.

In particular, embodiments where a mathematical model $f_{CR}$ is used to calculate, from signal IPA, a first value R representative of the patient's ratio $R^r=CR^r/G^r$, and, by multiplication of this first value by a blood glucose value $G^r$ measured by sensor 101, the patient's estimated insulin sensitivity factor CR (according to the above-mentioned formula $$CR(t)=G^r(t) \times R(t)=G^r(t) \times f_{CR}(IPA(t))).$$

As a variant, mathematical model $f_{CR}$ may be a model two input variables enabling to directly calculate the estimated factor CR from signal IPA and a blood glucose value $G^r$ measured by sensor 101, according to the following formula:

$$CR(t)=f_{CR}(IPA(t),G^r(t))$$

For each patient, function $f_{CR}$ then is a function of equation:

$$f_{CR}(IPA,G^r)=a \times IPA^b + c \times G^{rd} + e$$

where a, b, c, d, and e are patient-specific parameters, parameters b and d corresponding to the orders of the model. As an example, parameters b and d are set to be equal to 1, the model then being a linear model.

Further, the described embodiments are not limited to the specific embodiment of a blood regulation system described in relation with FIGS. 1 and 3, that is, a predictive control system using a mathematical model to predict the future trend of the patient's blood glucose and accordingly adjust the insulin doses to be delivered to the patient. More generally the provided method of real time estimation of the patient's insulin sensitivity factor CR, from signal IPA and a single blood glucose value measured on the patient, may be implemented in any blood glucose regulation system capable of taking advantage of an in situ and real time estimate of the patient's insulin sensitivity factor.

The invention claimed is:

1. An automated system for controlling a patient's blood glucose, comprising a blood glucose sensor, a device for measuring a physical activity of a patient, and a processing and control unit, wherein:
   the processing and control unit is configured to generate, by convolution of a signal PA supplied by the device for measuring a physical activity of the patient with a decreasing mathematical function H, a signal IPA representative of the influence of the patient's physical activity on his/her insulin sensitivity; and
   the processing and control unit is configured to calculate, from a first patient-specific mathematical model $f_{CR}$ and taking into account signal IPA and from a single blood glucose value $G^r$ measured by the sensor, a factor CR representative of the patient's insulin sensitivity.

2. The system according to claim 1, further comprising an insulin injection device, wherein the processing and control unit is configured to control the insulin injection device by taking into account factor CR.

3. The system according to claim 2, wherein the processing and control unit is configured to predict, from a second mathematical model, the future trend of the patient's blood glucose over a prediction period, and to control the insulin injection device by taking the prediction into account.

4. The system according to claim 1, in the first mathematical model is a function of equation $$CR=f_{CR}(IPA,G^r)=a \times IPA^b + c \times G^{rd} + e$$

where a, b, c, d, and e are patient-specific parameters.

5. The system according to claim 1, wherein the first mathematical model is a function of equation $$CR=G^r \times fR(IPA)=G^r \times (a \times IPA^b + c)$$

where a, b, and c are patient-specific parameters.

6. The system according to claim 1, wherein the processing and control unit is configured to implement a step of automatic calibration of first model $f_{CR}$ by taking into account a history of the blood glucose measured by the sensor, a history of insulin injected to the patient, a history of carbohydrate ingestion by the patient, and a history of the patient's physical activity signal PA over a past observation period.

7. The system according to claim 6, wherein the processing and control unit is configured to, during the automatic calibration step, measure a plurality of values of the patient's real insulin sensitivity factor $CR^r$ during a plurality of measurement events contained in the past observation period.

8. The system according to claim 7, wherein each measurement event corresponds to a continuous time range from an initial time $t_{init}$ to a final time $t_{final}$, complying with the following criteria:
   time $t_{init}$ is in a hyperglycemia phase, that is, a phase where the patient's blood glucose is greater than a predetermined threshold;
   a correction bolus, that is, an additional insulin dose has been delivered to the patient after the beginning of the hyperglycemia phase and before time $t_{init}$, to limit the duration of the hyperglycemia phase;
   the patient's blood glucose continuously decreases between initial time $t_{init}$ and final time $t_{final}$; and
   no carbohydrate ingestion by the patient has occurred between time $t_{init}-T_j$ and time $t_{final}$, where $T_j$ is a predetermined fasting duration.

9. The system according to claim 7, wherein the processing and control unit is configured to, during the automatic calibration step, determine the first mathematical model $f_{CR}$ by regression from said plurality of values of the real insulin sensitivity factor $CR^r$.

10. The system of claim 1, wherein function H is a decreasing exponential function.

11. The system according to claim 1, wherein the measurement device comprises a user interface via which the patient declares his/her physical activities.

12. The system according to claim 1, wherein the measurement device comprises one or a plurality of sensors capable of measuring quantities representative of the patient's physical activity.

13. The system according to claim 12, wherein the measurement device comprises a motion sensor and/or a heart rate sensor.

* * * * *